US007407494B2

(12) United States Patent
Boström et al.

(10) Patent No.: US 7,407,494 B2
(45) Date of Patent: Aug. 5, 2008

(54) DEVICE FOR DELIVERING MEDICAMENT

(76) Inventors: Anders Boström, Hummelvretsvägen 1, Ekero (SE) S-178 36; Stefan Loof, Sandfjardsgatan 106, Arsta (SE) S-120 56

( * ) Notice: Subject to any disclaimer, the term of this patent is extended or adjusted under 35 U.S.C. 154(b) by 234 days.

(21) Appl. No.: 11/045,379

(22) Filed: Jan. 31, 2005

(65) Prior Publication Data

US 2006/0178630 A1 Aug. 10, 2006

(51) Int. Cl.
*A61M 5/00* (2006.01)
*A61M 37/00* (2006.01)

(52) U.S. Cl. .......................... 604/207; 604/85; 604/89; 604/211

(58) Field of Classification Search ................. 604/110, 604/187, 208, 209, 210, 218, 82, 89
See application file for complete search history.

(56) References Cited

U.S. PATENT DOCUMENTS 4,689,042 A * 8/1987 Sarnoff et al. ................. 604/89
6,793,646 B1 * 9/2004 Giambattista et al. ......... 604/90
2004/0210199 A1 * 10/2004 Atterbury et al. ........... 604/224
2006/0173408 A1 * 8/2006 Wyrick ....................... 604/110

* cited by examiner

*Primary Examiner*—Elizabeth R MacNeill

(57) ABSTRACT

A device for delivery of medicament includes a main housing, a container having at least two compartments, each containing a component of the medicament to be injected, and arranged to be connected to a patient delivery element, a longitudinally movable piston and a spring arrangement acting on the piston to exert a force on the components, a first holding element for holding the piston in a force-loaded state, and at least one activator for releasing the piston, a second holding element for stopping the piston when it has moved a certain first distance after one activation of the at least one activator and holding the piston in that position, wherein the force from the piston/spring arrangement and the movement causes the compartments to communicate with each other and the components to mix.

9 Claims, 19 Drawing Sheets

26 12 D 22 20 24 74 14 18 10

16
30
32
28
36
26
34

60
38
44
42
40

54
52
66
64

56
52
64
E
62
40
38
14

52
F
64
40
62

40
62
58
14
38

48
14

52
82
48

72
56
64
IXc
IXc
62
52
48
58
200

56
206
IXb
IXb
204
200

10
52
200
205
48
203
58
62

204
200
202

Fig. 16a
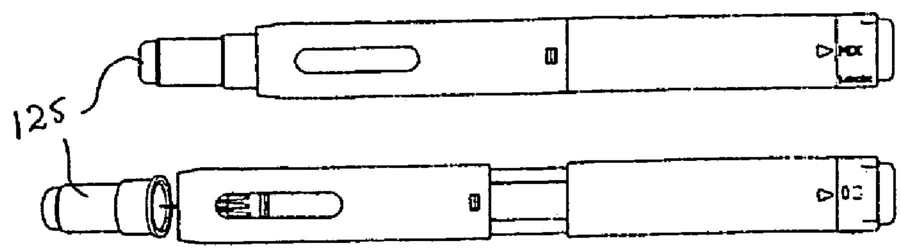
Fig. 16b
Fig. 16c
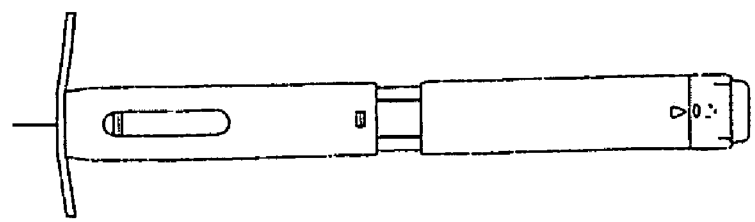
Fig. 16d
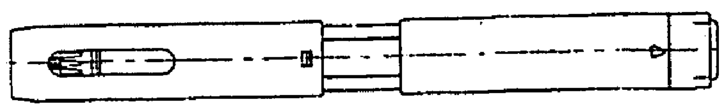
Fig. 16e 144
146
136
142
160
162
131
148
129
134
140
110
166
168
128
138
164
130
158
150
122
132
156
154
152
136
126
124
120
114
116
112
118
115
121

DEVICE FOR DELIVERING MEDICAMENT

FIELD OF TECHNOLOGY

The present invention relates to a device for delivering medicament to a patient and in particular in connection with medicament that needs to be pre-treated, mixed, before delivery.

BACKGROUND OF THE INVENTION

Different devices have during a number of years been more and more used for delivering medicament to a patient, such as auto-injectors, inhalers and such where the main reasons being the possibilities for the patients themselves to handle the delivery in an easy, safe and reliable way and also to facilitate the administration of drugs for hospital personnel in a quick, safe and reliable way. Depending on the intended use and the type of medicament, when looking at delivery of liquid drugs such as auto-injectors, they have developed varying degrees of automatic function, ranging from only automatic penetration or only automatic injection to fully automatic function including penetration, injection, withdrawal and shielding of the needle. A number of sub-functions have also been developed such as controlled injection rate, multiple doses with means for varying the quantity of each dose, locking of needle cover before and/or after use, and the like.

As regards the medicament, most types are packaged in cartridges, ampoules or syringes containing a ready-to-use liquid-state medicament, where the medicament is dissolved or suspended with the liquid, where they could be stored for a long time before use. However, some types of medicament cannot be pre-mixed because the medicament becomes degraded and looses its effect rather quickly when mixed with the liquid. Solutions can also have a limited effective time span. With such medicaments the user, patient or nurse/physician, has to perform the mixing within a limited time prior to the delivery. In the case of injecting the medicament, this is usually done such that the medicament in powder or liquid form is arranged in a container, often a small vial. An appropriate liquid is then poured into the vial, which may then need to be shaken in order to dissolve the medicament. A needle of a syringe is then inserted into the bottle and a quantity of the mix is drawn up, either the full content of the bottle or a certain part of it. This procedure is of course rather awkward, in particular for persons not used to handle these devices, and is obviously not suitable for auto-injectors.

In order to facilitate the mixing, cartridges, ampoules or syringes have been developed which contain two chambers, each containing a part of the medicament solution, which, when mixed, forms the medicament to be delivered. The two chambers are sealed off when stored in order that the medicament solution does not become degraded. When the medicament solution is to be mixed, passages are opened between the chambers, usually by depressing the stopper and in turn the divider of the syringe somewhat. The passages allow the mixing of the parts and the medicament is ready for delivery. Up to now these dual chamber cartridges, syringes or ampoules have only been used with ordinary type, manually handled devices. For certain applications and medicaments however, it would be advantageous to use a device in combination with these dual chamber solutions in an easy and user-friendly way in order to obtain the mixing before delivery.

BRIEF DESCRIPTION OF THE INVENTION

The aim of the present invention is to provide a medicament delivery device which facilitates the use of plurality-chamber cartridges, syringes, ampoules and other containers.

This aim is solved by the present invention characterised by claim 1. Additional advantageous developments of the present invention are characterised by the dependent claims.

According to one major aspect of the invention it is characterised by a device comprising a main housing, a container including at least two compartments, wherein each compartment contains at least one component of the medicament solution to be injected, and arranged to be connected to a patient delivery means, a longitudinally movable piston and a spring arrangement acting on said piston and capable of exerting a force on said components, a holding means arranged and capable of holding said piston in a force-loaded state, and at least one activator means capable of releasing said piston, characterised in that it further comprises stop means capable of stopping the movement of said piston when it has moved a certain first distance after one activation of the at least one activator means, wherein the force from the piston/spring arrangement and the movement causes the compartments to communicate with each other and the components to mix, and wherein, upon a subsequent activation of said at least one activator means, the piston moves a certain second distance, wherein the force from the piston/spring arrangement and the movement causes the mixed components to be ejected through the patient delivery means.

According to a further aspect of the invention, it comprises means for adjusting the second distance in order to adjust the second and subsequent distance in order for doses to be delivered.

The advantages with the present invention are several compared to the state of the art. Because the device is capable of stopping the piston acting on the stopper of the container or syringe with two or more chambers, the mixing can be performed in a very simple and yet reliable way and without the need of reloading the device for subsequent injections. The piston/spring arrangement has such a force and travel that both the mixing movement and the subsequent injections movements can be obtained.

The locking of the piston after the mixing may be obtained in many suitable ways and the release of the piston after the mixing procedure may be performed manually by pressing a button or the like or be performed automatically when, in the case of injectors, pressing the injector against the delivery site.

Because of this, the whole procedure of pre-mixing in external containers and transferring the mixed solution into a delivering device is completely removed, which is of convenience for all users and of specific benefit for patients having difficulties administering such devices and procedures, like elderly, very sick or children.

Regarding dose delivery, in contrast also to conventional devices where it could be difficult to deliver the proper, required dose, the device of the present invention is very easy to handle due to the dose adjusting capabilities presented. The patient merely sets the device to deliver the proper dose. It is of course possible with the present device to have a fixed dose that cannot be altered, which may be advantageous if for example children are to use it, or if it is desired to have a very easy-to-use functionality.

When used as an injector, the injector preferably is provided with a needle shield that is capable of covering the needle after use, which needle shield is locked in that position. This prevents accidental needle-sticks on contaminated needles from occurring.

These and other aspects of and advantages with the present invention will become apparent from the following detailed description and from the accompanying drawings.

BRIEF DESCRIPTION OF THE DRAWINGS

In the detailed description of non-limiting examples of the invention reference will be made to the accompanying drawings, of which

DETAILED DESCRIPTION OF THE INVENTION

Figure 1A:
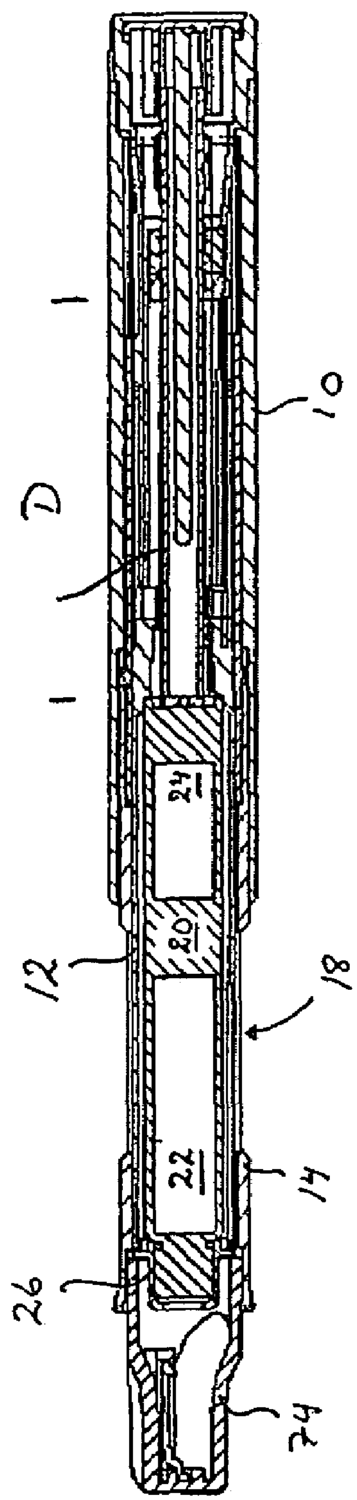
FIG. 1*a* is a longitudinal cross-sectional view of a first embodiment according to the invention in a state when it is delivered to the patient.

The present invention will now be described in detail in connection with an injector. It is if course possible to utilise the present invention in other delivering devices such as inhalers and the like devices arranged for delivering doses of medicament. The first embodiment of the invention shown in the drawings 1-8. In the detailed description reference is made to the "front" and "rear" of the device which is to be understood such that "front" is intended to be the end of the device where medicament is delivered, to the left in the figures, and "rear" is the opposite end of the device.

The injector comprises a main rear generally tubular housing 10 and a main front tubular housing 12. The front housing is surrounded by a generally tubular needle shield 14 slidable in relation to the front housing but held in a fixed rotational position by longitudinal ridges on the inner surface of the needle shield and corresponding grooves 16 on the outer surface of the front housing, FIG. 1*b*. The needle shield is further provided with windows 18. A syringe or cartridge 20 with two chambers 22, 24 is arranged inside the lower housing.

Figures 1B, 1C, 1D:
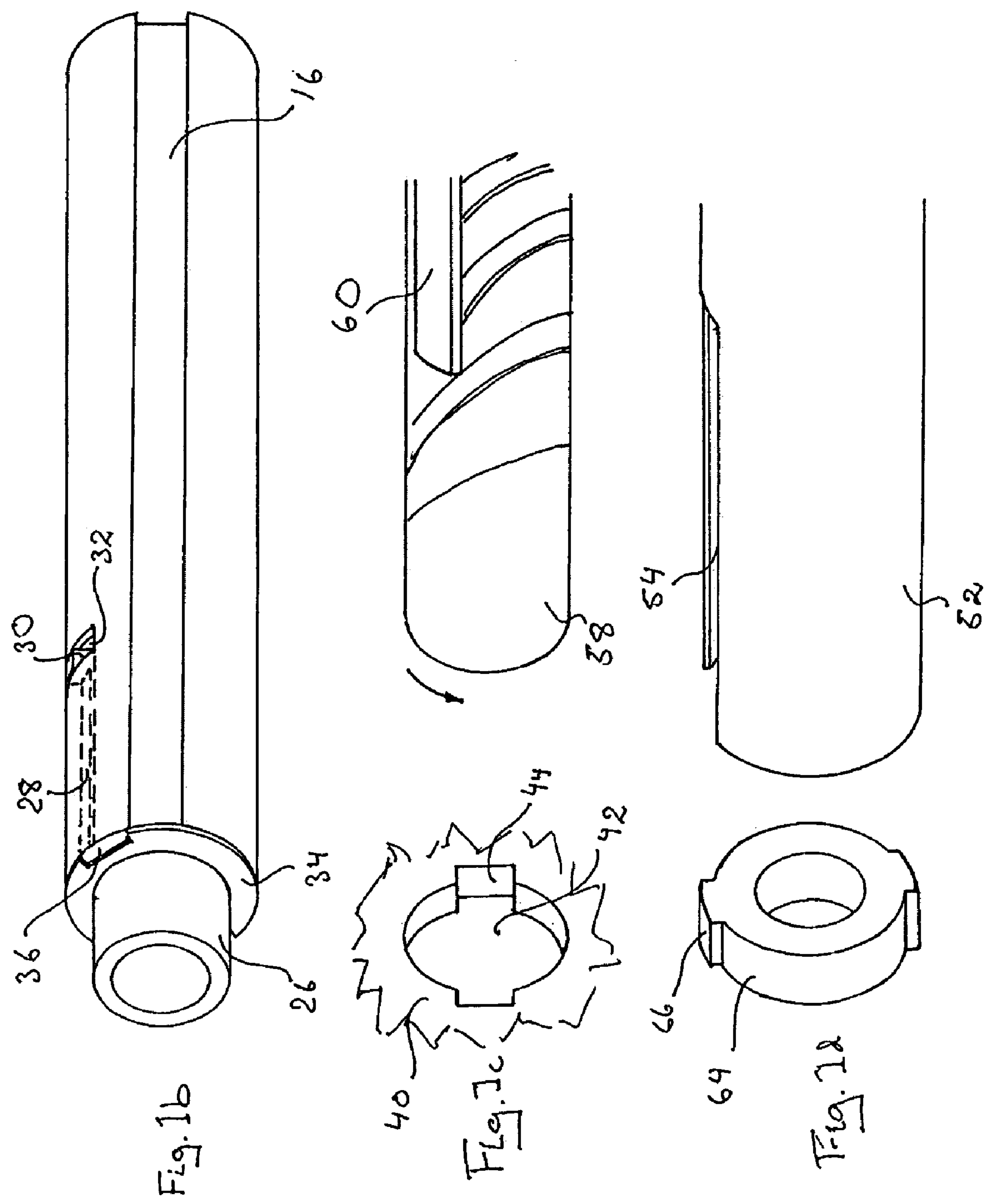
FIGS. 1*b*-1*d* are detailed views of certain components of the device of FIG. 1*a,*

To the front end of the front housing a neck portion 26 is attached with two tongues 28, one shown with broken lines in FIG. 1*b*, extending into the front housing 12, which tongues are arranged with outwardly directed protrusions 30, which in turn fit into recesses 32 arranged along a certain sector of the inner circumference of the lower housing. The neck portion 26 further comprises a plate 34 where the outer edge of the plate fits into a groove arranged on the ridges of the inner surface of the needle shield 14 and where the edge of the plate is arranged with cut-outs 36 corresponding in size to the grooves on the outer surface of the front main housing. A needle 38 can be attached to the neck portion in a manner which will be described below. Further the rear part of the front main housing is arranged with a wall 40 arranged with a central circular opening 42 having two opposite cut-outs 44, FIG. 1*c*. The upper part of the needle shield is arranged with openings 46.

Inside the rear housing a generally tubular guide sleeve 48 is slidably arranged and is provided with outwardly directed protrusions 50, that are engaging the openings 46 of the needle shield 14 so as to form a fixed connection between the two parts.

Inside the guide sleeve a further sleeve 52, hereafter named dose setting sleeve, is arranged. At its front end the dose setting sleeve is arranged with longitudinal grooves 54, FIG. 1*d*. At its upper end the sleeve is attached to, or made in one piece with, a dose setting knob 56, which knob extends out of the main rear housing 10, and is preferably provided with a grip means like grooves or protrusions as well as dose indication means, which will be explained later.

Inside the dose setting sleeve, a piston 58 is arranged which extends through the central opening 42 of the wall 40. The piston is attached to the dose setting knob 56. The piston is arranged with external, double helix threads, ie. one left-handed thread and one right-handed thread.

The piston is further arranged with longitudinally extending ribs 60, FIG. 1*c*. Two nuts 62, 64 are threaded onto the piston 58, hereafter named front nut 62 and rear nut 64, where one nut has right-handed threads and one nut has left-handed threads. The nuts are arranged inside the dose setting sleeve 52 such that they are prevented from rotating by the longitudinal grooves 54 of the dose setting sleeve 52 and ledges 66 on the outer surfaces of the nuts 62, 64 that fit into the grooves. Inside the piston a spring (not shown) is arranged between an end wall 68 of the piston and an abutment wall 70 of the dose setting knob 56. A guide rod 72 for the spring is attached to the dose adjusting knob.

The device according to the first embodiment is intended to function as follows. The device is delivered to the patient as seen in FIG. 1. The two nuts 62, 64 have been threaded onto the piston 58 with a certain distance D from the wall 40. The nuts are held in that position by the ledges 66 of the nuts fitting into the longitudinal grooves 54 of the dose adjusting sleeve, wherein the piston rests against the rear end of the medicament cartridge 16 and the spring is tensioned. The piston is prevented from moving forward in that the front end of the longitudinal ribs 60 is abutting the wall 40.

Figure 2:
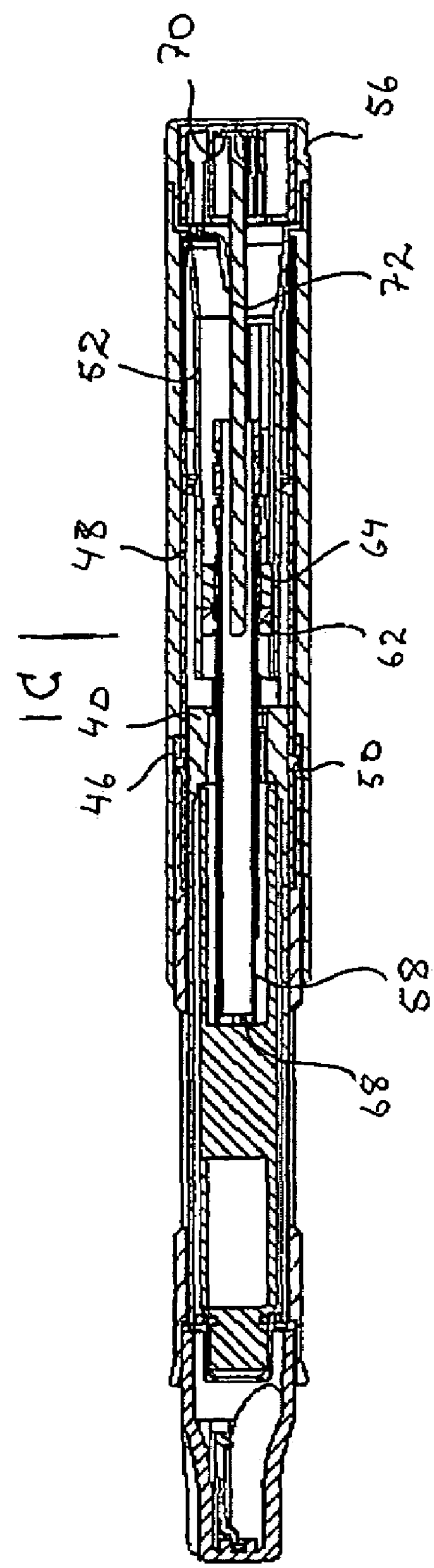
FIG. 2 is a view corresponding to FIG. 1 where a mixing has been performed.

In order to prepare the device for an injection the patient turns the dose setting knob 56 to a position "Mix" indicated on the outside of the upper main housing 10. The turning causes the piston 58 attached to the dose setting knob to be turned until its longitudinal ribs 60 are in register with the cut-outs 44 of the wall 40 whereby the piston moves forward due to the force of the spring, FIG. 2. This causes the stopper and divider of the cartridge 20 to move forward whereby passages are opened between the two compartments 22, 24 and the medicament component or components form is mixed with the liquid. The mixing can be viewed through the windows 18. Due to the built up pressure of the mixed medicament and gas or air the piston is prevented from moving further. The initial position of the nuts on the piston and the length of the piston are chosen such that after the mixing the nuts are positioned a certain distance C from the wall 40, FIG. 2 and also to obtain a proper mixing of the medicament.

Figure 3:
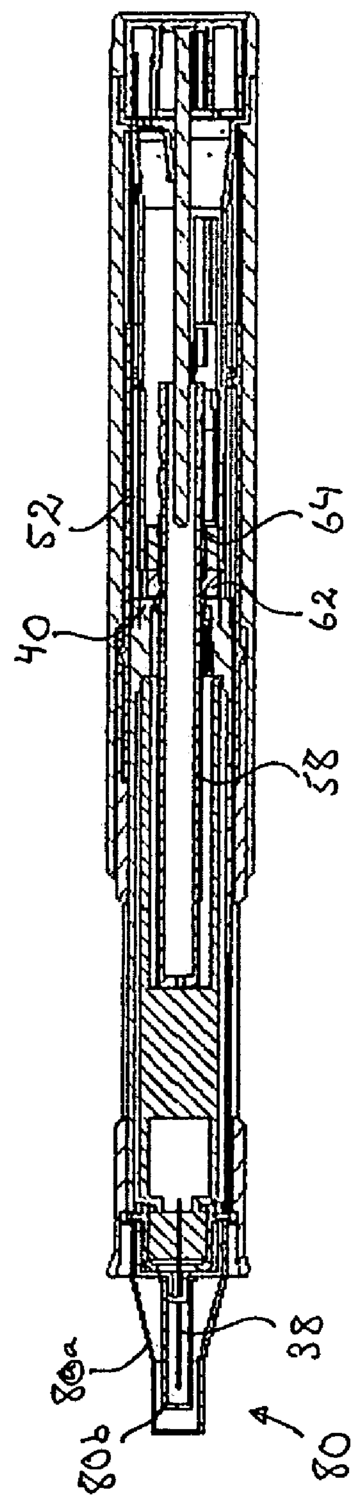
FIG. 3 is a view corresponding to FIG. 1 where a priming has been performed.
Figure 4:
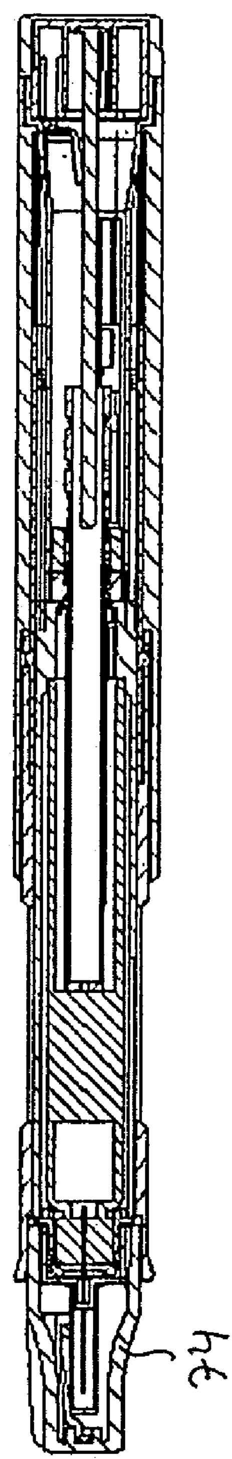
FIG. 4 is a view corresponding to FIG. 1 where a needle cover is removed and a tool is applied for activating the device.

A needle 38 with a needle cover 80, which needle cover preferably comprises an outer needle cover 80*a* and an inner needle cover 80*b* is attached onto the neck portion 26 of the main front housing, FIG. 3, whereby the rear end of the needle penetrates an elastic seal at the front end of the cartridge. Due to the pressure of the medicament in the cartridge, gas or air and a small amount of liquid is ejected from the compartment, and is collected and seen in the outer needle cover 80*a*, causing a priming of the device and resetting of the system in that the ejection of the medicament causes the piston 58 to move forward until the front nut 62 abuts the wall 40 and the rear nut 64 to be in contact with the front nut. The length of the dose setting sleeve 52 is such that when the front nut 62 is in contact with the wall 40 the ledges 66 of the front nut have moved out of the longitudinal grooves 54 of the dose setting sleeve 52. The device is now calibrated and reset in that the cartridge is ready for injection and the nuts are pushed together by the full force of the spring, thereby eliminating all play and other mechanical deficiencies of the mechanism.

Figures 5, 6:
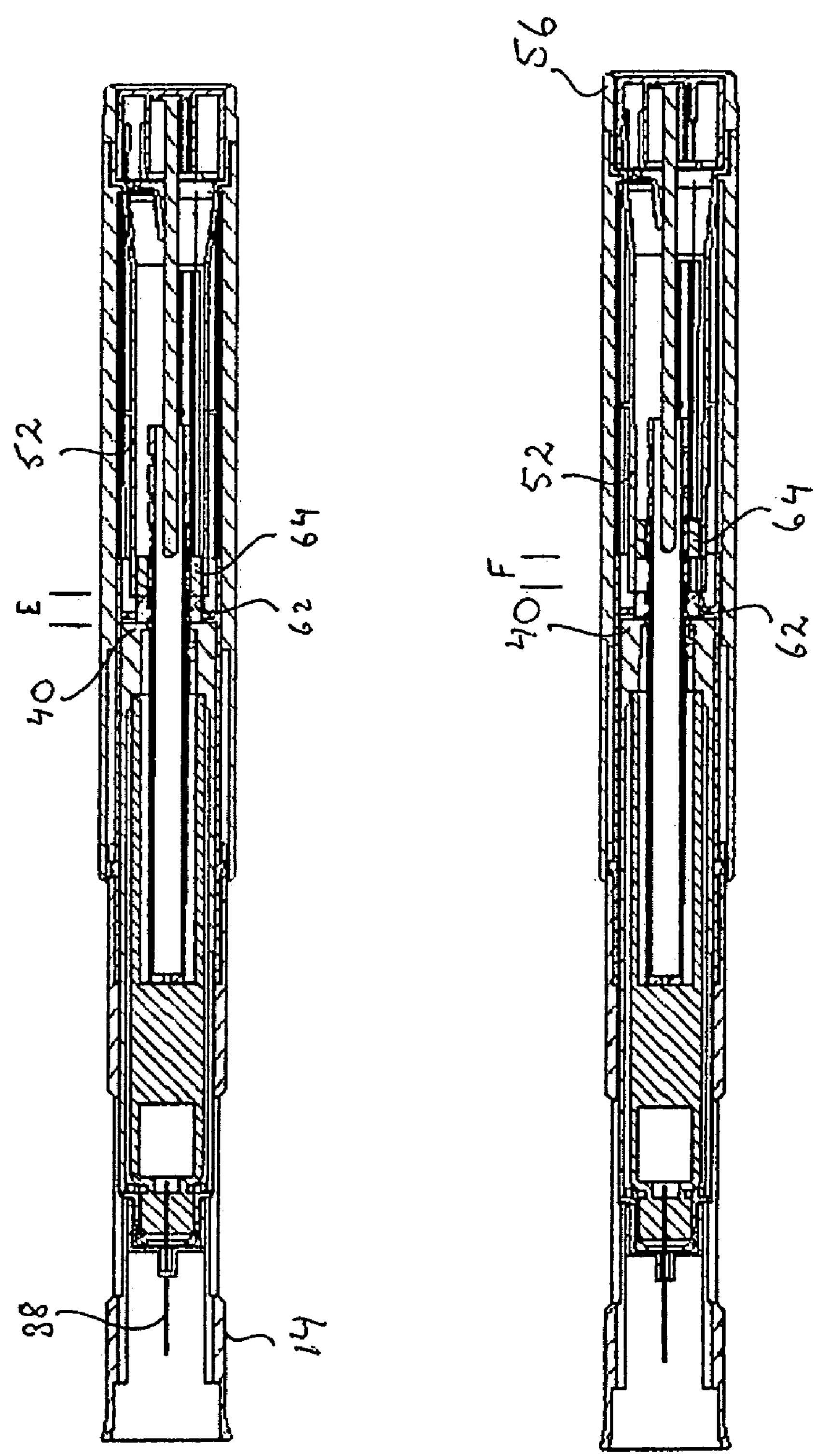
FIG. 5 is a view corresponding to FIG. 1 where the dose is activated and a needle cover has been pushed forward.
FIG. 6 is a view corresponding to FIG. 1 where a dose has been set.
Figure 11:
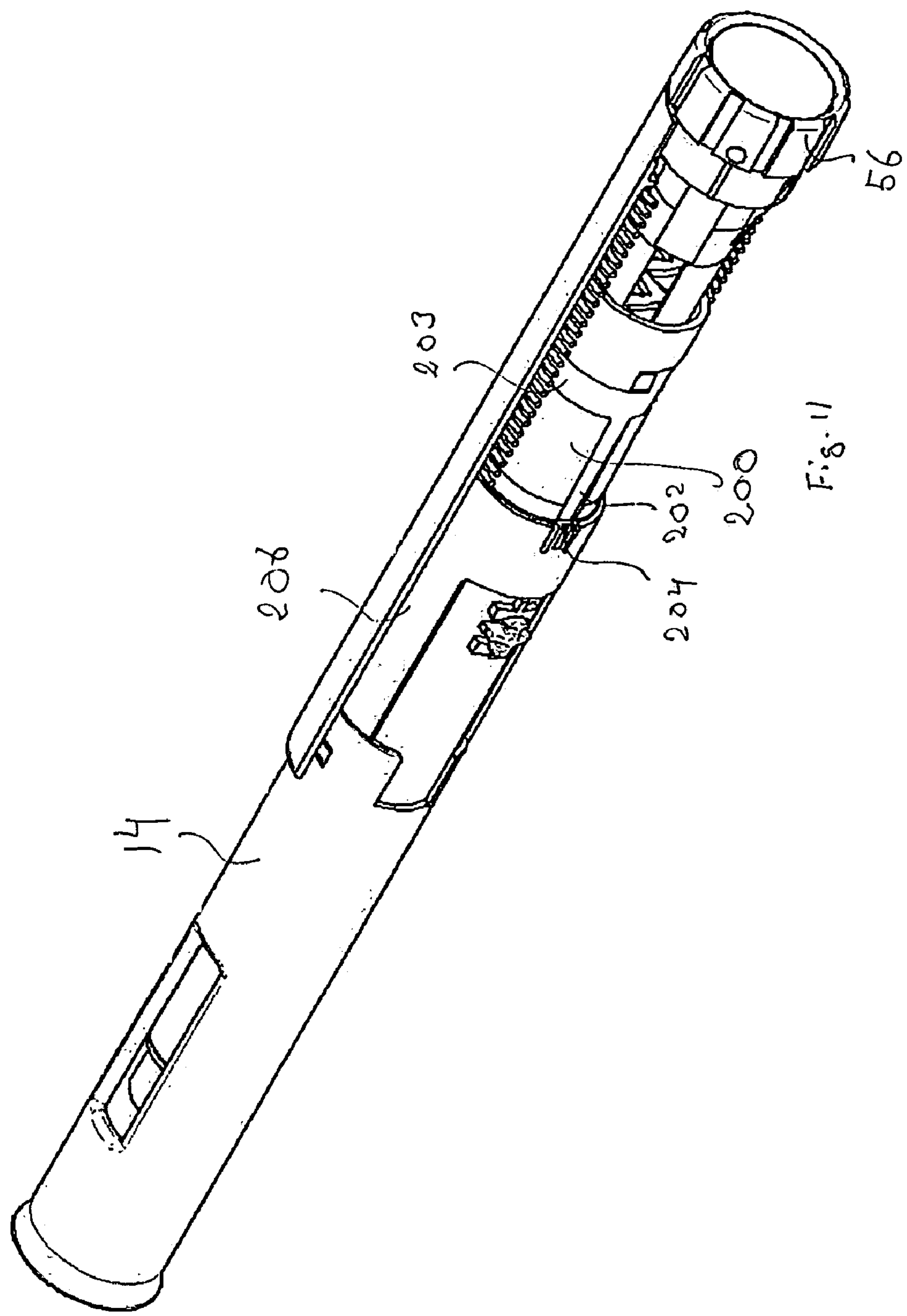

The outer needle cover 80*a* is now removed. In order to remove the inner needle cover and to be able to set a dose a tool 74, having a generally tubular end form designed to fit into the end of the needle shield 14, and further having protrusions at its end surface fitting into corresponding recesses in the plate 34 of the neck portion 26, is inserted into the end of the needle shield and turned, FIG. 11. This causes the plate 34 of the neck portion to be turned until its cut-outs 36 are in register with the groove 16 of the front housing, releasing the needle shield 14 and bringing it forward, surrounding the needle 38, by a spring (not shown), FIG. 5. When the tool is removed, it brings with it the inner needle cover.

The dose can now be set by turning the dose setting knob so that a dose quantity indication for the chosen dose on the outside of the main upper housing is in register with an indication mark on the knob.

The turning of the knob causes the dose setting sleeve also to turn. As can be seen on FIG. 5 the inner end of the dose setting sleeve 52 does not reach all the way to the wall 40 thereby creating a distance E, between the wall 40 and the end of the sleeve, which distance is somewhat larger than the width of the front nut 62, so that the front nut is no longer held by the sleeve. However the front nut is prevented from rotation by inwardly extending protrusions on the rear part of the needle shield. The turning of the knob 56 and the sleeve 52 causes the rear nut 64 to turn because of its ledges positioned in the groove and to move along the piston due to its threads in engagement with the threads of the piston. This creates a distance F between the nuts, FIG. 6.

The device is now ready for injection. The needle shield 14 is pressed against the injection site and the needle 38 is pushed into the patient, FIG. 7. When the upper end of the needle shield has moved into the main rear housing a certain distance the inwardly directed protrusions of the rear end of the needle shield 14 are moved out of engagement with the ledges of the front nut 62, which thus is released and will rotate due to the contact with the wall 40 and due to the force on the threaded piston 58 from the spring, whereby the piston will move into the cartridge and inject the medicament through the needle. The movement of the piston is stopped when the rear nut comes in contact with the front nut and the injection is completed. It is then to be understood that the distance F corresponds to a certain volume of medicament that is to be injected.

Figures 7, 8, 8A:
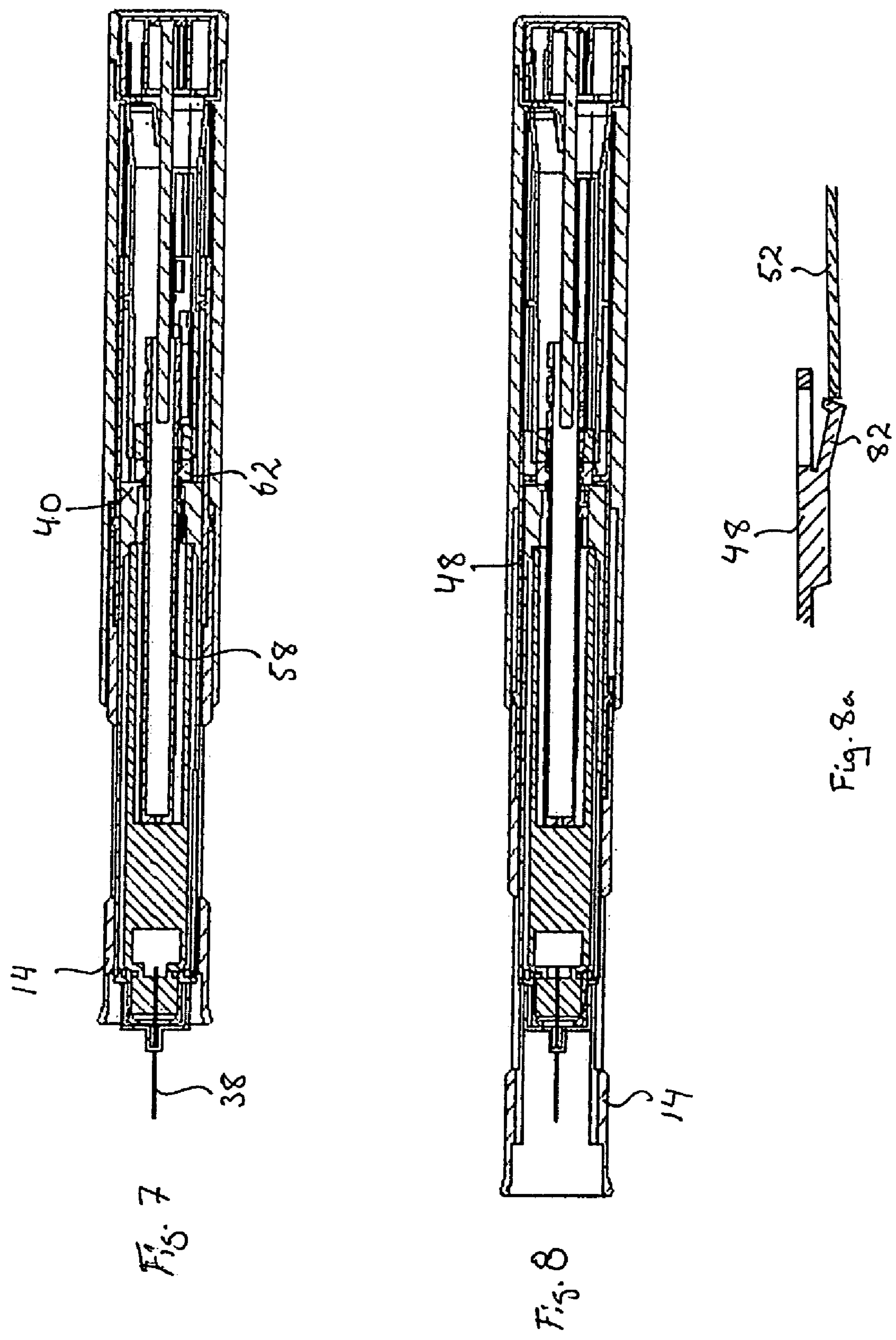
FIG. 7 is a view corresponding to FIG. 1 where the injection is activated.
FIG. 8 is a view corresponding to FIG. 1 after completed injection and withdrawal of the device.

The device can now be removed from the injection site, FIG. 8, whereby the needle shield 14 and the guide sleeve 48 are pushed forward by a spring (not shown) in order to cover the needle and locks in that position by resilient arms 82 arranged at the rear end of the guide sleeve 48 that pass the front end of the dose setting sleeve 52 when the needle shield has reached its most extended position, whereby the arms will move inwards and rest on the front end of the dose setting sleeve, FIG. 8*a*.

A variant of the design according to FIGS. 1-8 is shown in FIGS. 9-22.

Figures 9A, 9B, 9C:
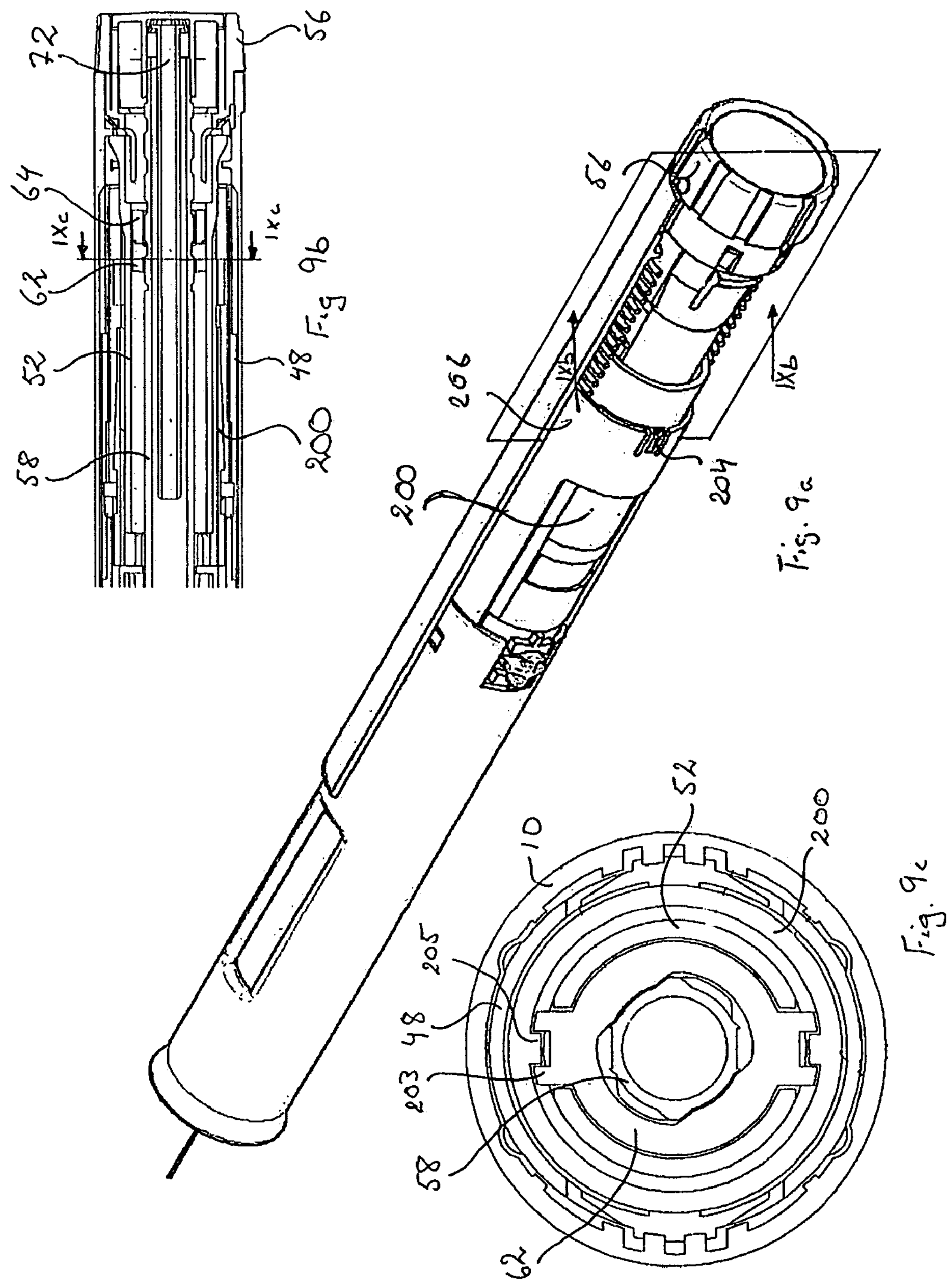
FIG. 9*a* is a somewhat modified design of the embodiment according to FIGS. 1-8.
FIG. 9*b* is a detailed view taken along the plane IXb-IXb in FIG. 9*a,*
FIG. 9*c* is a cross-sectional view taken along the line IXc-IXc in FIG. 9*b,*
Figure 10:
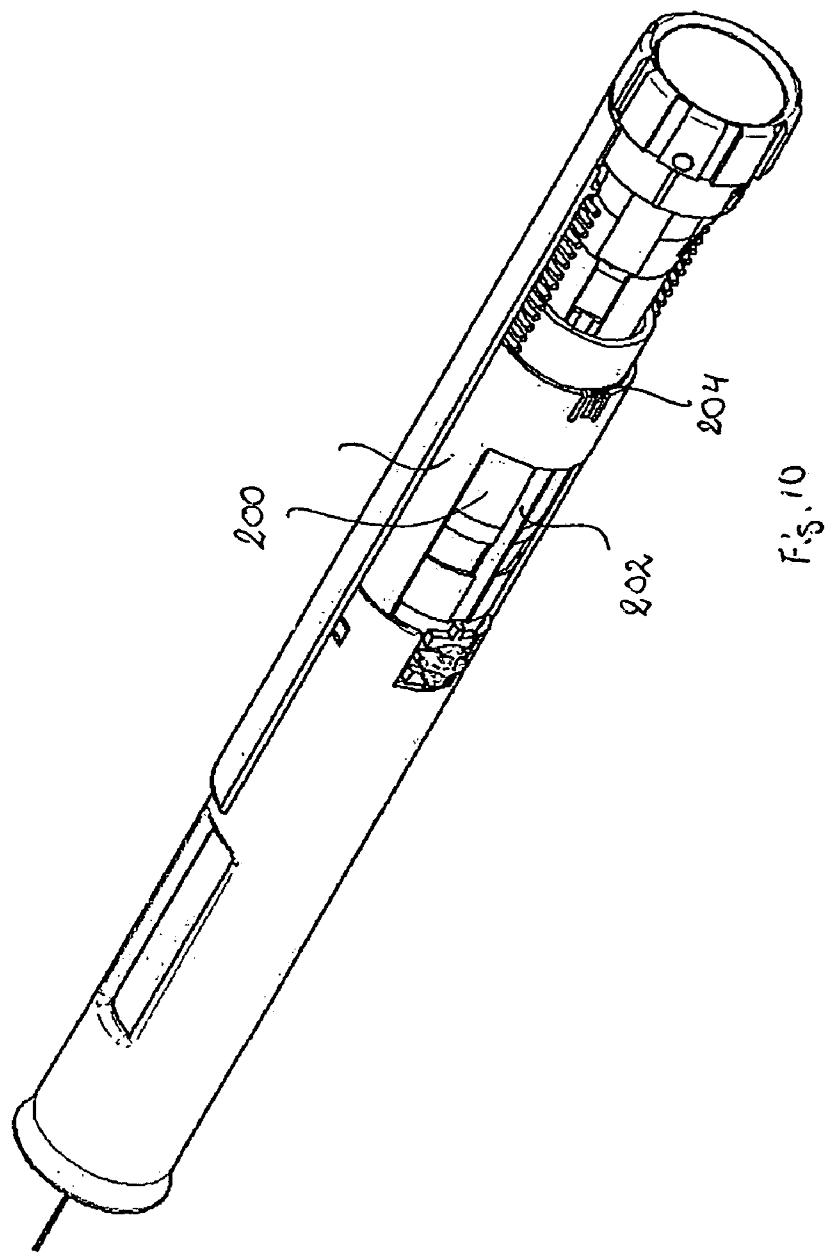
FIGS. 10-15 show the embodiment according to FIG. 9*a*, in different modes of operation, FIGS. 16 *a*-*e* are side-views of a second embodiment of the present invention in different steps of operation.

In this case a sleeve 200 is arranged and attached to the dose setting knob 56, having a particular configuration, FIG. 9. When in the initial delivery position inwardly gripping hooks 204 arranged on the inner upper surface of a shield link member 206, in turn attached to the needle shield 14, are in contact with an upper ledge 203, FIG. 11, arranged on the outer surface of the sleeve, thereby preventing any axial movement between the sleeve and the shield link member. When the injector is to be used the knob 56 is turned so that a mix position is indicated, FIG. 11.

The turning of the knob causes the piston 58 attached to the dose setting knob to be turned until its longitudinal ribs 60 are in register with the cut-outs 44 of the wall 40 whereby the piston moves forward due to the force of the spring and the mixing is performed, in the same manner as with the previous embodiment. The turning of the dose setting knob causes the dose setting sleeve 52, attached to the dose setting knob, to be turned. The turning of the dose setting sleeve turns the nuts 62, 64 because of their connection via the ledges 66 fitting into the grooves 54 of the dose setting sleeve. The front nut 62 is arranged with Y-shaped fork-like protrusions 203 that are in contact with ribs 205 arranged on the inner surface of the sleeve 200, which connection causes the sleeve 200 to be turned so that longitudinal grooves 202 on the outer surface of the sleeve is aligned with the hooks 204.

The step of attaching the needle and priming and resetting the device is also performed in the above described manner.

The outer needle cover 80*a* is now removed and the tool 74 is inserted into the end of the needle shield and turned as described above for preparing the device for injecting a dose. When removing the tool the inner shield is also removed.

Figure 12:
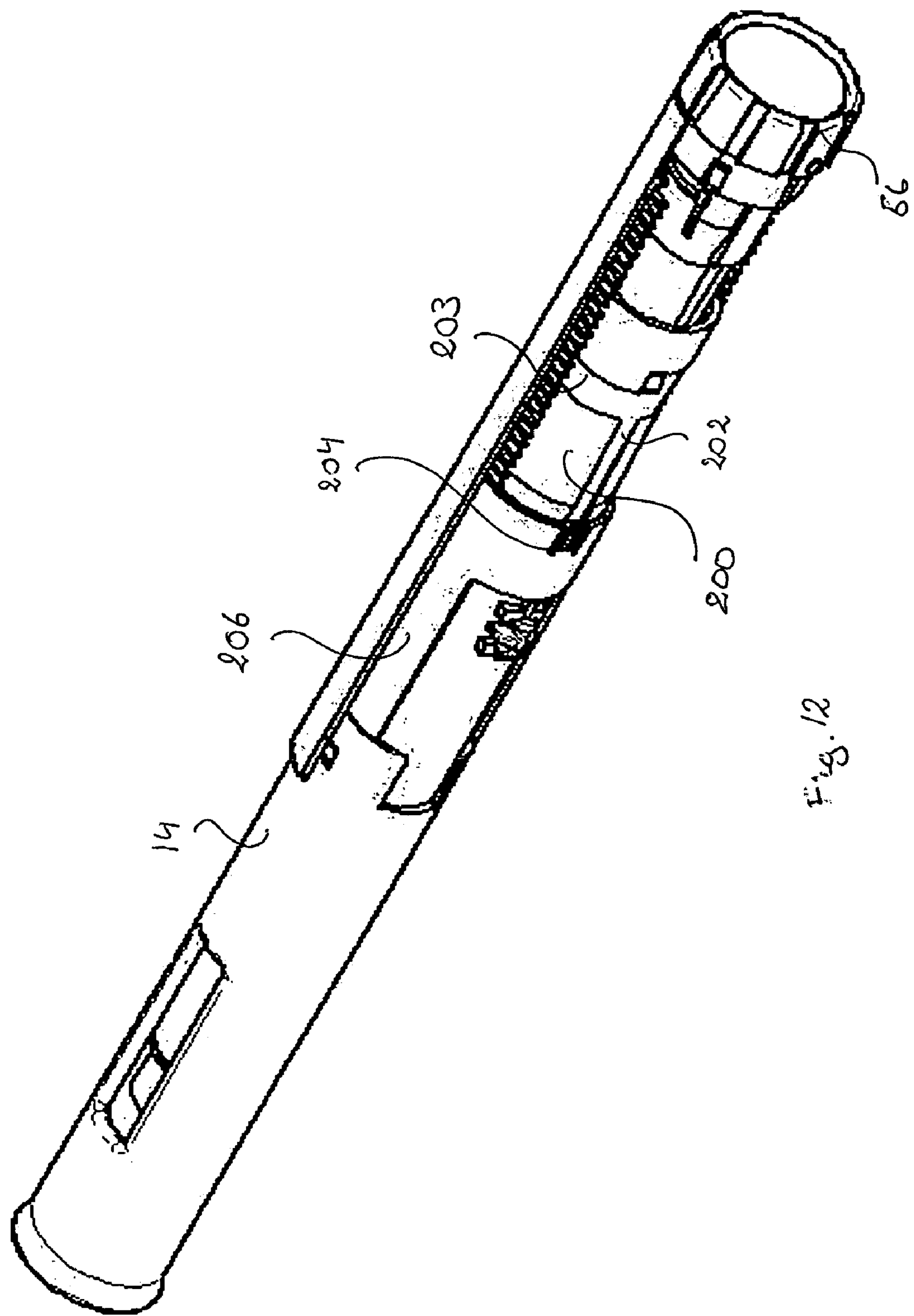
Figure 13:
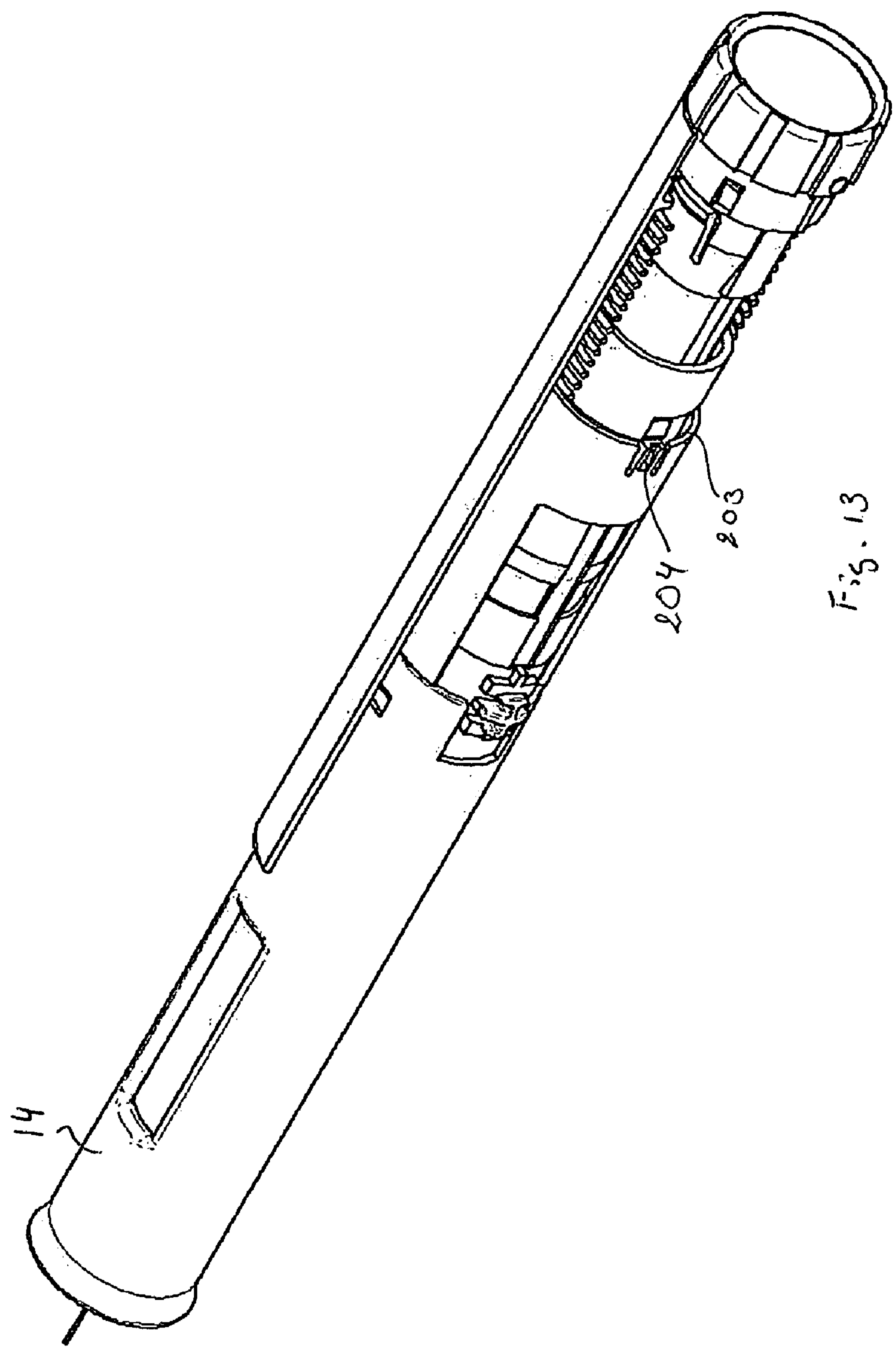
Figure 14:
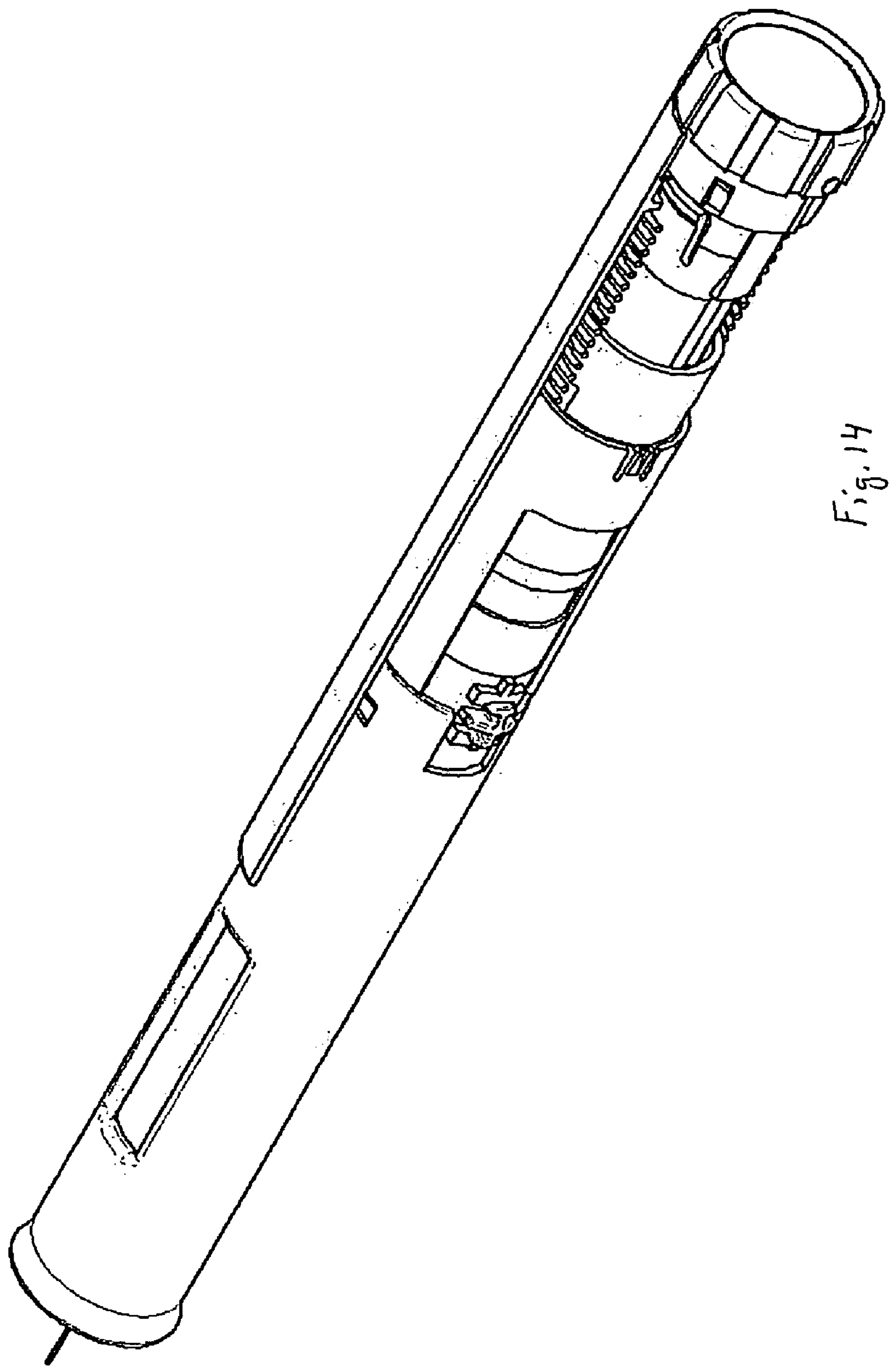

In order to prepare for a certain dose, the dose setting knob 56 is turned again, FIG. 12, whereby the nuts are separated in the same manner as in the previous embodiment because the dose setting sleeve will rotate the rear nut so that a certain distance is created between them. Next the front end of the injector is pressed against the injection site whereby the needle penetrates the skin. At the same time the needle shield 14 is pushed back, FIG. 13, whereby the hooks 204 of the needle shield link slide back in the grooves 202 until they are in their almost rearward position. At this position the grooves have terminated, FIG. 13. The leaving of the hooks from the grooves 202 and the annular groove 203 enables the sleeve 200 and thus the front nut to rotate, because of the connection between the two via the Y-fork and the ribs, whereby the front nut rotates on the threads of the piston, moving it forwards, which in turn causes an injection of the mixed medicament through the needle until the nuts are in contact with each other, as described previously, FIG. 14.

Figure 15:
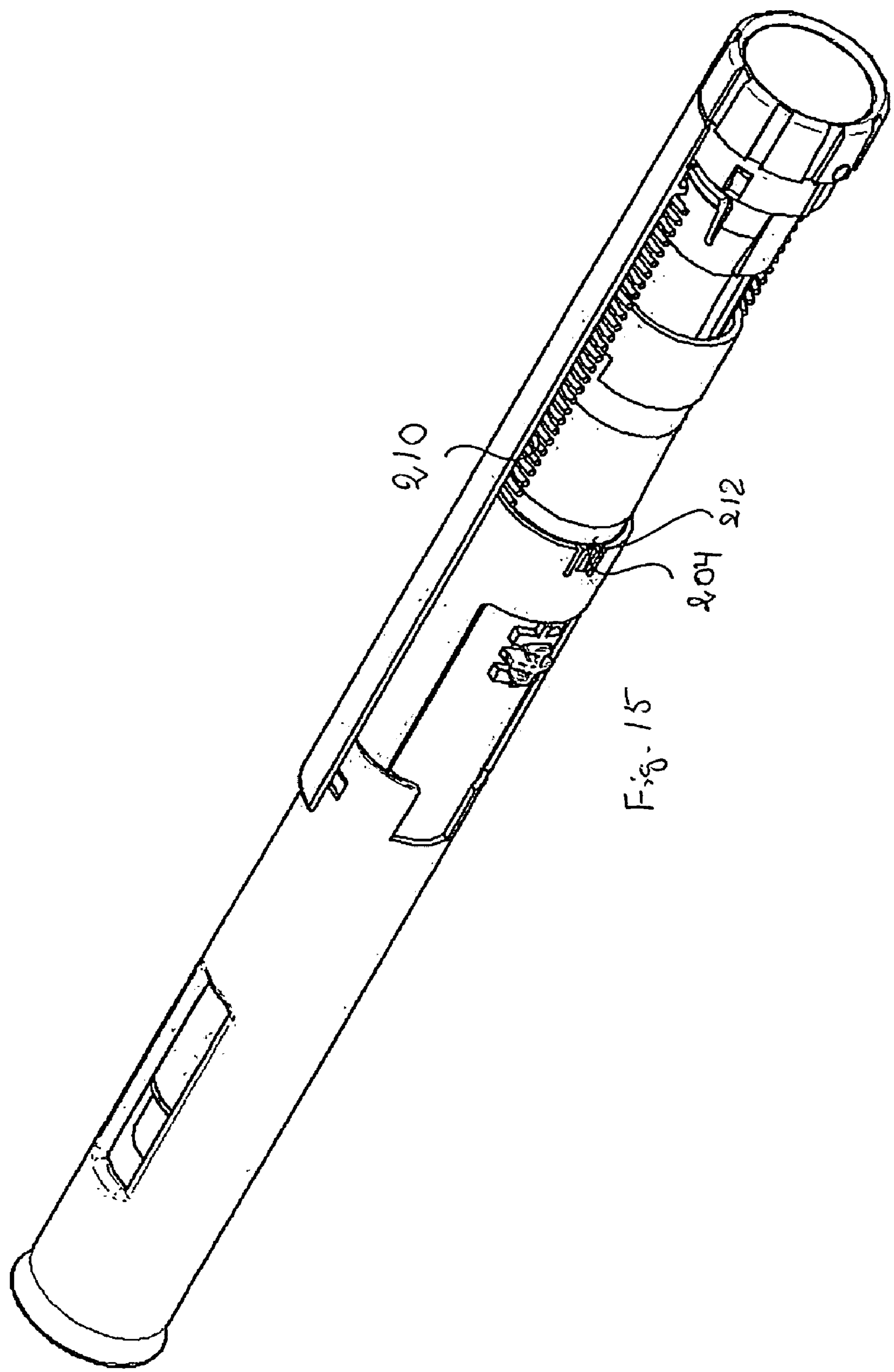

The injector is removed from the injection site, FIG. 15, whereby the needle shield spring 210 forces the needle shield forward, whereby the hooks 204 of the needle shield link to slide on the outer surface of the sleeve 200 until the needle shield is in its foremost position. In that position the hooks are placed in a front groove 212 arranged on the outside of the sleeve 200, whereby the rear surfaces of the hooks engage with the rear surface of the front groove, which in turn locks the needle shield from moving backwards.

A second embodiment of the present invention will now be described in connection with FIGS. 16 to 22. It includes a main rear generally tubular housing 110 and a main front generally tubular housing 112. The main front housing is surrounded by a generally tubular needle shield 114 arranged to be slidable along the lower housing. The needle shield is arranged with windows 115. Inside the main front housing a syringe or cartridge 116 with two chambers, 118, 120, is arranged. In the non-affected state the chambers each contain a component of the medicament solution to be injected, and the chambers are sealed off from each other.

The front end of the front main housing is arranged with a neck portion 121, onto which a needle may be attached. A needle shield holder 122 in the form of a generally tubular shape is arranged inside the rear main housing 110. It is connected to the needle shield holder 122 by protrusions 124 fitting into recesses 126 in the rear part of the needle shield, to the right in the figures. The rear part, also to the right, of the needle shield holder is arranged with inwardly directed protrusions 128. A spring 129 is arranged between a ledge 131 arranged on the inside of the main upper housing 110 and the upper end surface of the needle shield holder. Further a piston 130 extends through the centre of the rear main housing with one end abutting the inner end of the syringe 116. The piston is on its outer surface arranged with protrusions 132, 134 at certain locations along the piston. Inside the piston a dose actuation spring 136 is arranged, which is guided by a guide rod 138 at the upper end of the rear main housing. Surrounding the piston/spring assembly is a guide sleeve 140 having an elongated groove in which a stop ledge 142 arranged at the upper end of the piston 130 can slide, the function of which will be explained below.

An activator means 144 is arranged at the rear main housing comprising an activation button 146 located at the rear end of the device. The activator means further includes a sleeve-like part 148 surrounding the piston/spring assembly and the guide sleeve 140. The activator sleeve is also arranged with a groove in the same manner as the guide sleeve 140. A holding means 150 is arranged abutting a dividing wall 152 in the front main housing at its upper end. The dividing wall is arranged with a through-hole, through which the piston 130 protrudes. The holding means includes a number of resiliently flexing tongues 154 which are pressed inwards, and contact the outer surface of the piston due to their inherent resilient properties. In a non-activated state the lower part of the activator means is arranged near the holding means. The activator means further includes a deflecting means 156 arranged with to the left pointing protrusions 158 with inclined surfaces, where the lower part of the inclined surfaces are in contact with the outer ends of the resilient tongues 154.

Outside the actuator sleeve a dosage adjusting means 160 is arranged. It comprises an upper (to the right) adjusting part 162 which protrudes outside the upper end of the rear main housing 110 and has grip ribs or the like as well as indications for different adjusting positions, such as locked position, mixing, dose quantity and the like, as will be explained. The outer surface adjacent the adjusting part is provided with an indication, like an arrow, to function in conjunction with the adjusting indications. The dosage adjusting means further comprises a front part 164 extending inside the upper main housing and surrounding the actuator means. On the inside surface at its lower end it comprises a number of inwardly directed ledges 166 at different distances to the upper end of the dose adjusting means, the function of which is to provide different dose quantities, as will be explained later. The front part 164 is further provided with a outwardly projecting ledge 168 extending a certain distance along its periphery, on which ledge the protrusion 128 of the needle shield holder 122 is resting against the force of the needle shield spring 129.

The device according to the second embodiment is arranged to function as follows. In a delivery state, FIG. 16*a*, the injector is delivered without a needle and with the needle shield in a retracted position. The dosage adjusting means is in the "LOCK"-position wherein the device and the actuator button is locked. The piston 130 is held in position by the resilient tongues 154 resting against front protrusions 132 of the piston. The resilient tongues 154 are prevented from moving outwards by the position of the front part 64 of the dose adjusting means 160, FIG. 10.

Figure 17:
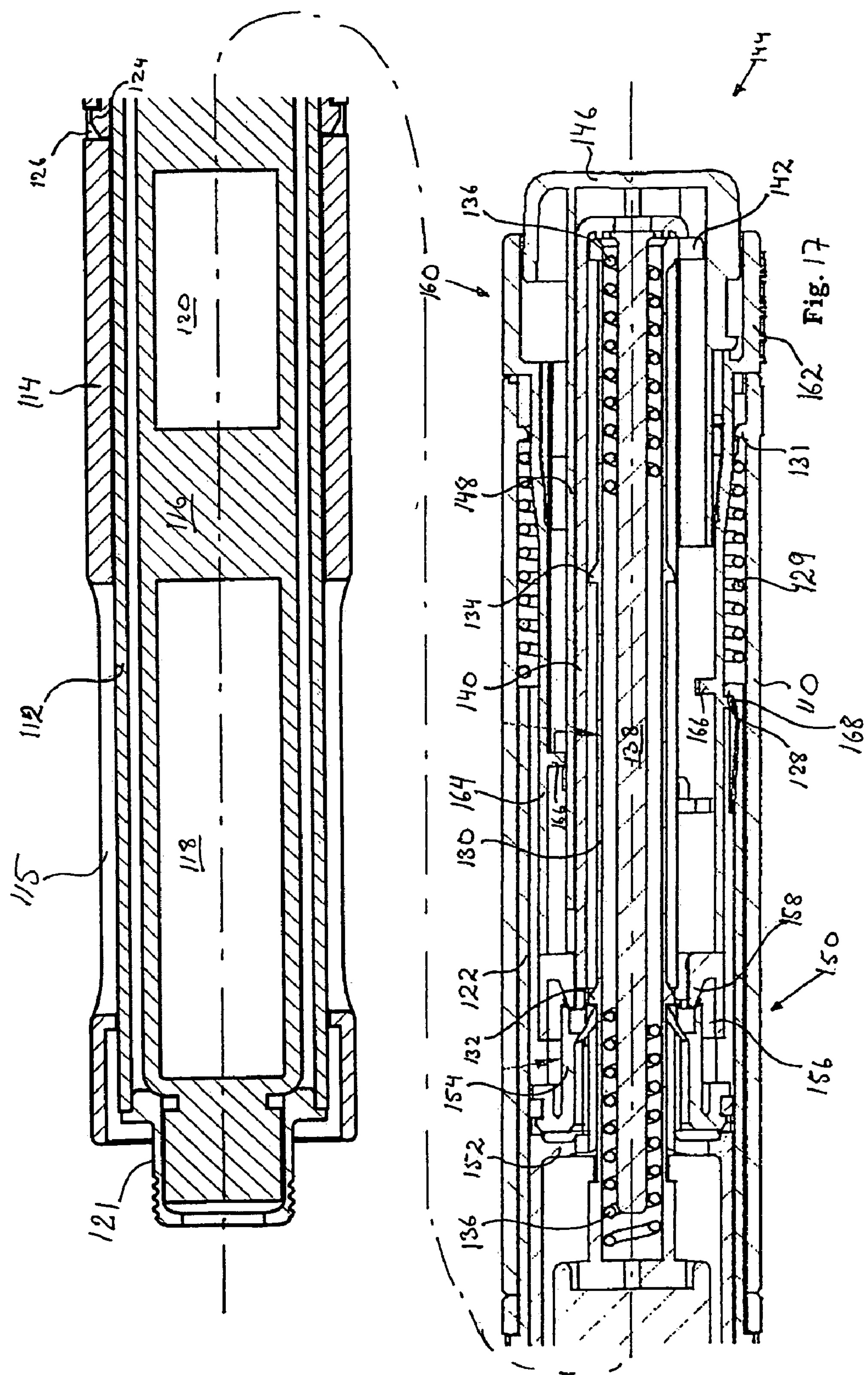
FIG. 17 is a side-view of the second embodiment of the invention.
Figure 18:
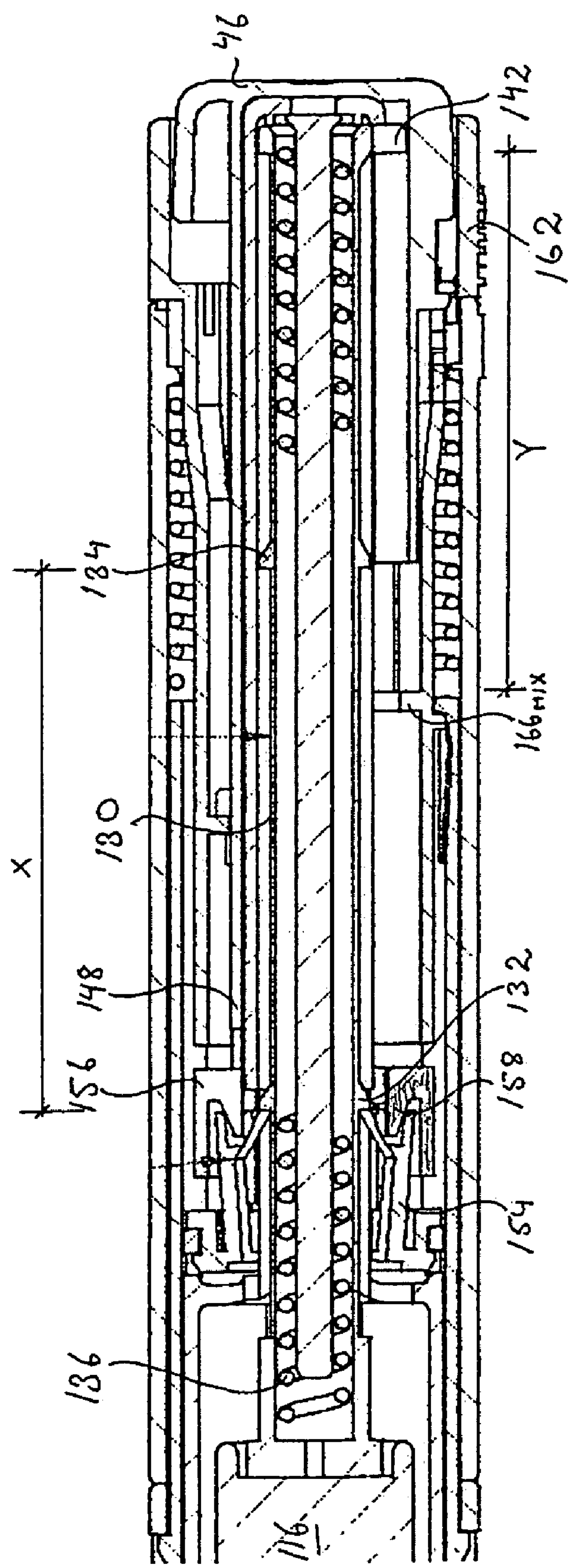
FIG. 18 is a partial view in cross-section of the upper end of the auto-injector according to the invention with actuating means in a non-activated mixing position.
Figure 19:
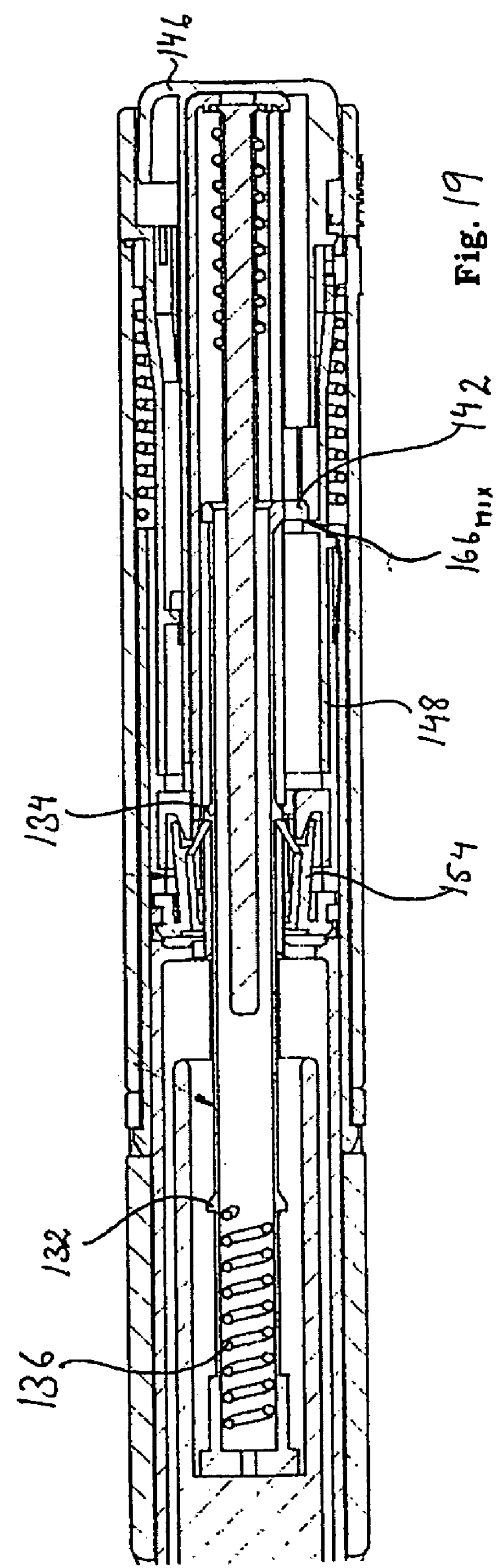
FIG. 19 is a view corresponding to FIG. 18 where mixing has been performed but an activation button is still depressed.

When a dose is to be delivered the dose adjusting means is firstly put in "MIX"-position by rotating the adjusting part 162, FIGS. 16*b* and 17, where the resilient tongues 154 are free to move but non-affected and the ledge corresponding to the mixing $166_{MIX}$ is facing the groove of the guide sleeve 140 and actuator sleeve 148, FIG. 18. When the actuator button 146 is depressed, FIG. 18, the front part 148 of the actuating means presses on the deflecting means 156 whereby the inclined surfaces of the protrusions 158 press the resilient tongues radially outward and out of contact with the front protrusions 132 of the piston 130, whereby this is moved to the left in the figures due to the spring 136, FIG. 19. This movement of the piston causes the plunger of the syringe 116 to be pressed inwards whereby a passage is opened between the two chambers of the syringe. Because of the passage the component in the rear compartment 120 is forced into the forward compartment 118 and the two components are mixed to a solution ready to inject. The patient can see the mixed solution through the window 115 of the needle shield 114. Because of the pressure built up in the mixed solution the piston is stopped after a certain distance, in which position the stop ledge 142 of the piston is at a short distance from the mixing protrusion $166_{MIX}$. When the piston 130 is in this position the upper protrusions 34 are adjacent the resilient tongues 154, which means that the distance X between the lower and upper protrusions of the piston is substantially equal to the distance Y between the stop ledge of the piston before activation and the mixing protrusion $166_{MIX}$ when in position. When the actuator button is released the resilient tongues will move into contact with the piston again.

The next step is to attach a needle, FIG. 16*b*. This is done by attaching a needle/needle cover assembly to the neck 121 of the device, eg. by threading it onto the neck or by some other suitable means, preferably holding the device vertically with the needle pointing upwards. When the inner end of the needle enters the front chamber now containing the mixed solution, possible air and a certain amount of the medicament will be ejected through the needle due to the pressure inside the chamber from the piston, so called priming. By this the piston is moved a short distance whereby the stop ledge 142 is in contact with the protrusion $\mathbf{166}_{MIX}$ and the resilient tongues 154 are resting against the rear protrusions 134, thereby preventing the piston from further movement, FIG. 19.

Figure 20:
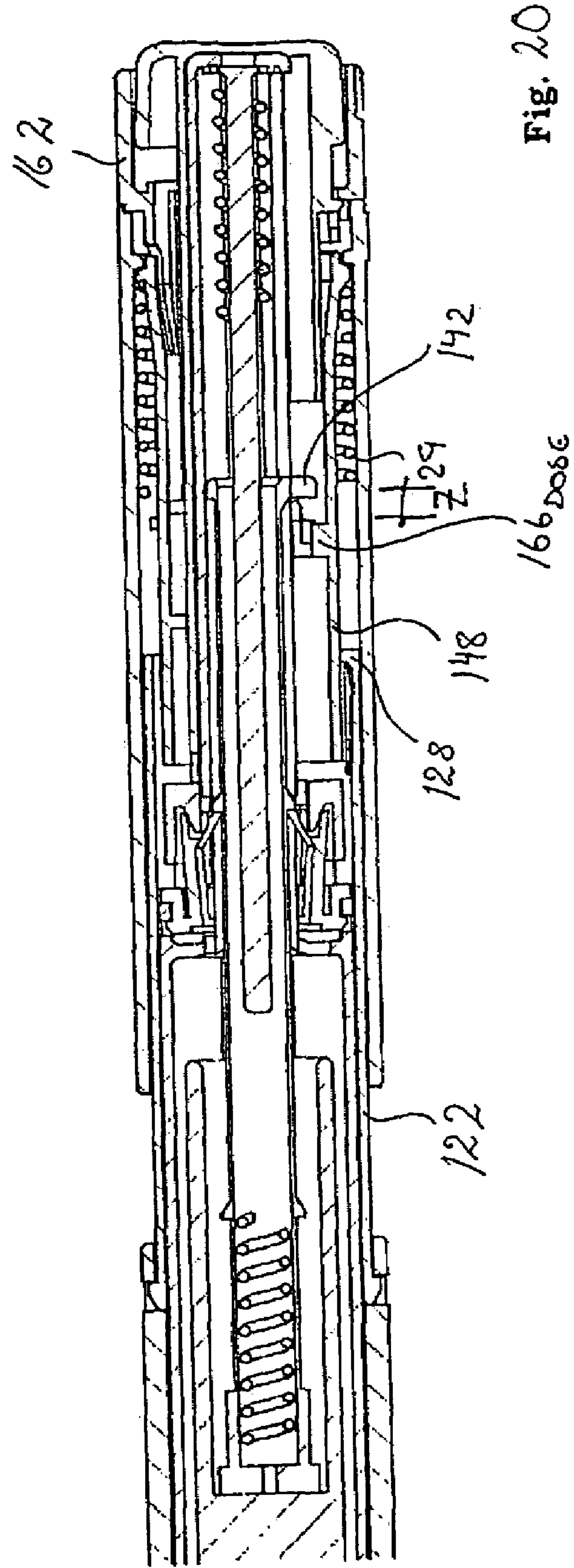
FIG. 20 is a view corresponding to FIG. 18 with a dose set.
Figure 21:
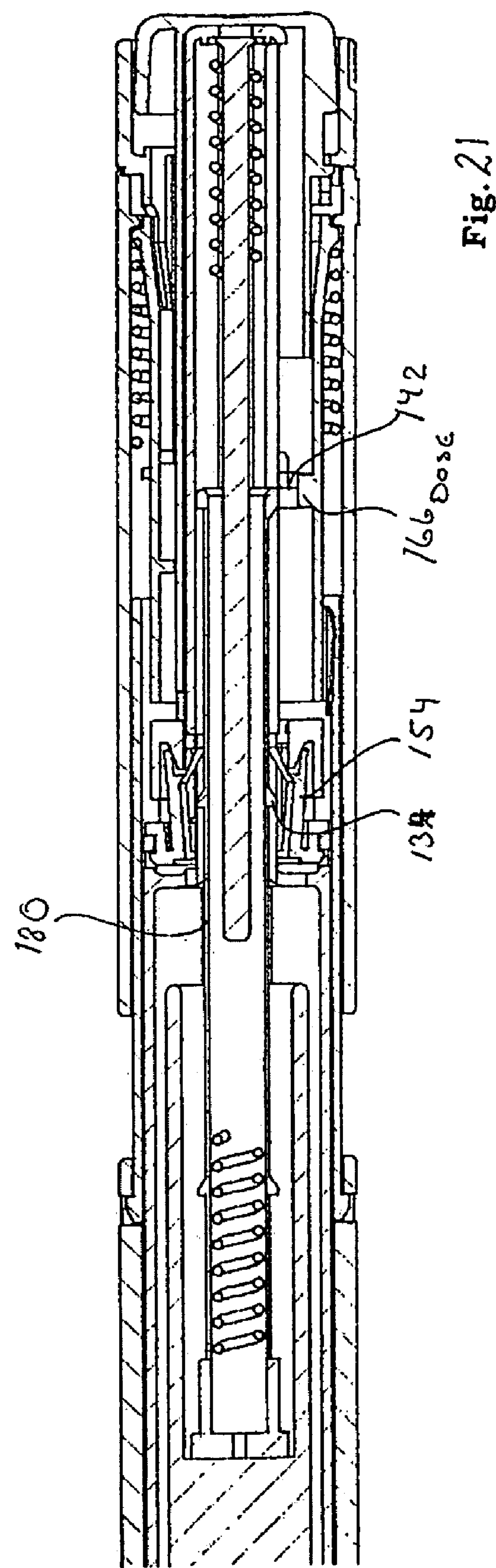
FIG. 21 is a view corresponding to FIG. 18 during injection.
Figure 22:
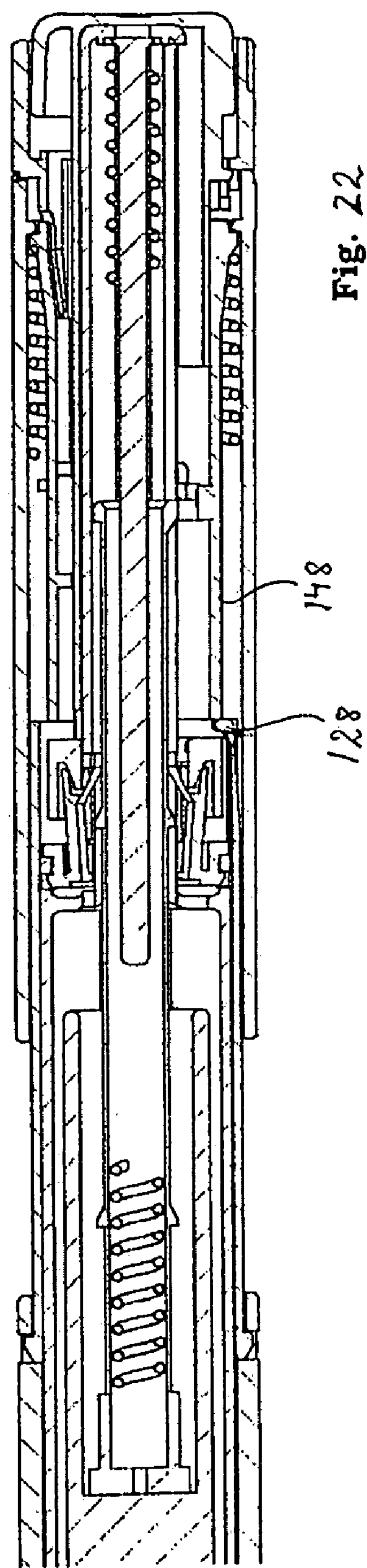
FIG. 22 is a view when the injector is withdrawn and the needle cover is pushed out around the needle and locked.

When the needle and needle cover are attached the patient then adjusts the dosage means to the dose quantity recommended by the physician. This is done by rotating the dose adjusting part 162, FIG. 20, so that the recommended quantity displayed on the outer surface of the dose adjusting part is aligned with the arrow on the main rear housing 110. The turning of the dose adjusting part could be guided by a tactile stop and release means between the turning components so that there are distinct positions for the dose adjusting part when a certain dose is set. The rotation of the dose adjusting part, and thus the lower adjusting means 148 causes its ledge 168 to move out of contact with the projection 128 of the needle shield holder, whereby it and thus the needle shield 114 is pushed forward, to the left in the figures, by the needle shield spring 129. The movement of the needle shield causes the needle cover 125 to be pushed off the needle, FIG. 16*c*. At the same time the needle shield 114 is moved forward such a distance as to cover the needle from view. The needle shield is however not locked in this position. Further the rotation of the doses adjusting part causes an inwardly directed protrusion $\mathbf{166}_{DOSE}$ corresponding to the desired dose to be positioned facing the groove of the guide sleeve 140 and actuator sleeve 148. FIG. 20. This also provides a distance Z, dose distance between the protrusion $\mathbf{166}_{DOSE}$ and the stop ledge 142.

The patient then penetrates the skin with the needle at the injection site whereby the needle shield is moved inwards against the force of the needle shield spring, FIG. 16*d*. This force also causes a stretching of the skin at the injection site. After that the patient depresses the activator button 146 whereby the front part of the actuating means presses on the deflecting means 156 whereby the inclined surfaces of the protrusions 158 press the resilient tongues radially outward and out of contact with the rear protrusions 134 of the piston 30, FIG. 21. The force of the spring urges the plunger rod to move the stopper and divider of the syringe to move, whereby the medicament is injected into the patient. The movement of the piston is stopped when the stop ledge 142 of the piston is abutting the dose protrusion $\mathbf{166}_{DOSE}$. The injection is now completed and the patient can withdraw the needle. During the withdrawal the needle shield is pushed forward by the spring 129, thereby covering the needle from view, FIG. 16*e*. When the needle shield has reached its forward most position it is locked in that the protrusions 128 of the needle shield holder fits into a space between the lower end of the lower part 148 of the dose adjusting means and the deflecting means 150, FIG. 22. This prevents unintentional needle sticks in that the needle shield is locked from movement. The injector may now be discarded.

Further conceivable embodiments of the present invention could comprise means for enabling the above described devices to be capable of delivering more than one injection dose. Even though the medicament, when mixed and ready to use, degrades with time and looses its properties, many of the solutions do not degrade so rapidly and may be used over a number of days. Preferably the device should then be able to deliver a number of doses and when appropriate of different quantities. The first described embodiment could for example be designed such that the second nut could be turned again after the first dose has been delivered, and after replacement of the needle, so that a distance is created between the nuts, which distance corresponds to the subsequent travel of the piston when released and thus the required and adjusted dose quantity.

Also, even though the embodiments described above are needle containing injection devices, the present invention may be applied to other types of devices where the medicament has to be pre-mixed before administration, such as needle-less injectors, inhalers, nebulizers and the like.

It is to be understood that the invention as described above and shown in the drawings is a non-limiting example and that the invention is defined by the patent claims. Thus, several parts of the described injector may be replaced with other part with the same or similar function as will be readily appreciated by the skilled man.

The invention claimed is:

1. Device for delivery of medicament comprising a main housing, a container including at least two compartments, wherein each compartment contains a component of the medicament to be injected, and arranged to be connected to a patient delivery means, a longitudinally movable piston and a spring arrangement acting on the piston and capable of exerting a force on the components, a first holding means arranged and capable of holding the piston in a force-loaded state, first activator means capable of acting on the first holding means for releasing the piston a certain first distance, wherein the force from the spring arrangement causes the piston to move the first distance, allowing the compartments to communicate with each other and the components to mix, a second holding means capable of stopping the movement of the piston when it has moved the first distance after one activation of the first activator means and holding the piston and the spring arrangement in that position, and dose adjusting means arranged and capable of interacting with the second holding means for adjusting a predetermined dose which corresponds to a second distance to be moved by the piston, wherein a second activator means is capable of acting on the second holding means for further releasing the piston, and wherein, upon a subsequent activation of the first activator means, the force from the spring arrangement causes the piston to move the second distance and eject the predetermined dose through the patient delivery means.

2. Device according to claim 1, wherein the first and second holding means comprise protrusions arranged on said piston and flexible holding members cooperating with said protrusions.

3. Device according to claim 1, wherein the first activator means comprises an activator button which upon being depressed, is capable of releasing the first and second holding means.

4. Device according to claim 2, wherein the dose adjusting means comprises a plurality of protrusions arranged adjacent said piston, where each protrusion is arranged at different axial distance, the piston comprises a ledge capable of cooperating with said plurality of protrusions, and means for aligning a selected one of said plurality of protrusions in the travel path of said piston, thereby defining said second distance.

5. Device according to claim 1, further comprising a needle shield arranged and capable of extending around the needle upon withdrawal of the injector from the injection site, and capable of locking in that extended position.

6. Device for delivery of medicament comprising:

a main housing;

a container including at least two compartments, wherein each compartment contains a component of the medicament to be injected, and arranged to be connected to a patient delivery means;

a longitudinally movable piston and a spring arrangement acting on the piston and capable of exerting a force on said components;

a first holding means arranged and capable of holding the piston in a force-loaded state;

first activator means capable of acting on the first holding means for releasing the piston, wherein the force from the piston/spring arrangement and the movement causes the compartments to communicate with each other and the components to mix;

a second holding means capable of stopping the movement of the piston when it has moved a certain first distance after one activation of the first activator means and holding the piston in that position; and dose adjusting means arranged and capable of adjusting a second distance of the piston/spring arrangement in order to set a predetermined dose;

wherein a second activator means is capable of acting on the second holding means for releasing the piston; upon a subsequent activation of the first activator means, the piston moves the second distance; the force from the piston/spring arrangement and the movement causes the mixed components to be ejected through the patient delivery means; and the second holding means comprises threads arranged on said piston, a first and a second nut threaded on said piston, and an abutment wall arranged adjacent said piston, against which the nuts abut when the piston has moved the first distance, means for displacing the second of said nuts in relation to the first nut axially along said piston, wherein said second holding means is capable of holding said first nut, and wherein the second activator means comprises a front end of said device capable of being movable axially upon penetration of said device into a patient, which axial movement causes said second holding means to release said first nut and hold said second nut, where the force of the piston/spring arrangement causes the first nut to rotate and the piston to move.

7. Device according to claim 6, wherein the means for displacing said second nut constitutes a dose adjusting means and the axial displacement of said second nut corresponds to said second distance.

8. Device according to claim 6, wherein the dose adjusting means comprises a plurality of protrusions arranged adjacent the piston, where each protrusion is arranged at different axial distance, the piston comprises a ledge capable of cooperating with the plurality of protrusions, and means for aligning a selected one of the plurality of protrusions in the travel path of the piston, thereby defining the second distance.

9. Device according to claim 6, further comprising a needle shield arranged and capable of extending around the needle upon withdrawal of the injector from the injection site, and capable of locking in that extended position.

* * * * *